(12) United States Patent
Hooper et al.

(10) Patent No.: US 11,464,939 B2
(45) Date of Patent: *Oct. 11, 2022

(54) WEARABLE APPARATUS

(71) Applicant: EMPATHIC TECHNOLOGIES LTD., London (GB)

(72) Inventors: Jack Christopher Hooper, Leceister (GB); Fotini Georgia Markopoulou Kalamara, Oxford (GB); Nell Bennett, Maidstone (GB); Andreas Timothy Bilicki, Pairs (FR)

(73) Assignee: Empathic Technologies Ltd., London (GB)

( * ) Notice: Subject to any disclaimer, the term of this patent is extended or adjusted under 35 U.S.C. 154(b) by 169 days.

This patent is subject to a terminal disclaimer.

(21) Appl. No.: 16/701,300

(22) Filed: Dec. 3, 2019

(65) Prior Publication Data

US 2020/0171269 A1 Jun. 4, 2020

Related U.S. Application Data

(63) Continuation of application No. 15/116,693, filed as application No. PCT/GB2015/050180 on Jan. 27, 2015, now Pat. No. 10,532,181.

(30) Foreign Application Priority Data

Feb. 4, 2014 (GB) ..................................... 1401909
Jan. 9, 2015 (GB) ..................................... 1500305

(51) Int. Cl.
*A61M 21/02* (2006.01)
*A61B 5/024* (2006.01)
(Continued)

(52) U.S. Cl.
CPC ......... *A61M 21/02* (2013.01); *A61B 5/02438* (2013.01); *A61B 5/486* (2013.01);
(Continued)

(58) Field of Classification Search
CPC ... A61B 5/02438; A61B 5/4836; A61B 5/486; A61H 2201/123; A61H 23/04;
(Continued)

(56) References Cited

U.S. PATENT DOCUMENTS 4,702,231 A 10/1987 Arpin
6,637,485 B1 10/2003 Sartena
(Continued)

FOREIGN PATENT DOCUMENTS

CN 1143490 A 2/1997
CN 1163152 A 10/1997
(Continued)

OTHER PUBLICATIONS

Communication in European Patent Application No. 15 702 550.3, dated Mar. 20, 2018.
(Continued)

*Primary Examiner* — Christine H Matthews
(74) *Attorney, Agent, or Firm* — Venable LLP

(57) ABSTRACT

A wearable apparatus capable of altering a physiological parameter such as the heart rate of a user to provide a relaxing or stimulating effect on the user is provided. The apparatus comprises a device capable of engaging the patient's skin to provide a rhythmic tactile stimulus to the user that can alter the user's heart rate and an arrangement for securing the device to the user such that the device can apply the stimulus to the user. The apparatus may be part of a system enabling the device to be controlled remotely. The apparatus may also be configured to provide additional tactile stimuli.

24 Claims, 10 Drawing Sheets

(51) Int. Cl.
  *A61B 5/00* (2006.01)
  *A61N 1/36* (2006.01)
  *A61H 23/04* (2006.01)
  *A61M 21/00* (2006.01)

(52) U.S. Cl.
  CPC ........... *A61B 5/4836* (2013.01); *A61H 23/04* (2013.01); *A61N 1/36014* (2013.01); *A61H 2201/123* (2013.01); *A61M 2021/0022* (2013.01); *A61M 2021/0027* (2013.01); *A61M 2021/0044* (2013.01); *A61M 2021/0061* (2013.01); *A61M 2021/0072* (2013.01); *A61M 2205/0294* (2013.01); *A61M 2205/3303* (2013.01); *A61M 2205/8206* (2013.01); *A61M 2209/088* (2013.01); *A61M 2210/04* (2013.01); *A61M 2230/06* (2013.01); *A61M 2230/65* (2013.01)

(58) Field of Classification Search
  CPC .. A61M 2021/0022; A61M 2021/0061; A61M 21/02; A61M 2210/04; A61M 2230/06
  See application file for complete search history.

(56) References Cited

U.S. PATENT DOCUMENTS

| | | | |
|---|---|---|---|
| 7,060,041 | B1 | 6/2006 | Weil et al. |
| 10,532,181 | B2* | 1/2020 | Hooper ................ A61B 5/4836 |
| 2002/0117115 | A1 | 8/2002 | Helwig |
| 2003/0181116 | A1 | 9/2003 | Van Heerden et al. |
| 2004/0034289 | A1 | 2/2004 | Teller et al. |
| 2004/0162587 | A1 | 8/2004 | Hampton et al. |
| 2004/0216787 | A1 | 11/2004 | Shim |
| 2005/0215846 | A1 | 9/2005 | Elliott |
| 2008/0027694 | A1 | 1/2008 | Gitman |
| 2008/0319279 | A1 | 12/2008 | Ramsay et al. |
| 2010/0204595 | A1 | 8/2010 | Marx |
| 2010/0268297 | A1 | 10/2010 | Neisz |
| 2011/0172500 | A1 | 7/2011 | Van Dooren et al. |
| 2011/0310613 | A1 | 12/2011 | Evans et al. |
| 2013/0023722 | A1* | 1/2013 | Kruk ................ A61M 5/14244 446/72 |
| 2013/0123570 | A1 | 5/2013 | Ly et al. |
| 2013/0171599 | A1 | 7/2013 | Bleich et al. |
| 2014/0357960 | A1* | 12/2014 | Phillips ................ A61B 5/318 600/301 |

FOREIGN PATENT DOCUMENTS

| | | |
|---|---|---|
| CN | 1471984 A | 2/2004 |
| CN | 201727828 U | 2/2011 |
| CN | 102056535 A | 5/2011 |
| CN | 202699824 U | 1/2013 |
| DE | 33 12 801 A1 | 10/1984 |
| DE | 100 41 944 A1 | 9/2001 |
| EP | 0339471 A2 | 11/1989 |
| FR | 1237702 A | 8/1960 |
| JP | 2006-055625 A | 3/2006 |
| WO | 93/01861 A1 | 2/1993 |
| WO | 2010/121592 A1 | 10/2010 |

OTHER PUBLICATIONS

English translation of Aug. 2, 2018 Office Action in Chinese Patent Application No. 20150018591.8.
Search Report in U.K. Patent Application No. GB1401909.5, dated Aug. 28, 2014.
International Search Report and Written Opinion of the International Searching Authority in PCT/GB2015/050180.
Search Report and Feb. 1, 2021 Communication in European Patent Application No. 19 21 3994.
Dec. 9, 2021 Office Action in Chinese Patent Application No. 201910442215.1 (with English translation).

* cited by examiner

WEARABLE APPARATUS

TECHNICAL FIELD

The present invention relates to a wearable apparatus and, in particular but not exclusively, to a wearable apparatus that can alter a person's heart rate by providing a stimulus impulse.

BACKGROUND TO THE INVENTION

Many devices are available for monitoring various physiological parameters such as heart rate and administering treatments. For example, US2010/0204595 discloses a heart monitoring system for treating a condition of a user exhibiting an abnormal heart rate. A heart rate monitor monitors one or more heart rate parameters of the user. A processor receives the parameters from the heart rate monitor and compares the parameters with threshold values in associated data storage and transmits a signal if the parameters exceed one or more of the threshold values. An audio device and a tactile device receive the signal from the processor. Responsive to the signal, the audio device provides an audible sound to the user while the tactile device provides a tactile sensation to the user. The audible sound and tactile sensation are adapted to treat the user's condition, alleviate symptoms of the condition, or combinations thereof. The tactile sensations are provided to the left and/or right hand side of the user's body to engage both sides of the user's brain.

There are many reasons why a person may want to alter their heart rate, be this for medical purposes, health and fitness reasons or mental state change. Other than treatments e.g. of the form described above, this is currently achieved through the use of drugs such as caffeine, or techniques such as meditation. However, these may take up a lot of time, be distracting or have further undesirable side effects.

Aspects and embodiments of the present invention have been devised with the foregoing in mind.

SUMMARY OF THE INVENTION

According to a first aspect of the present invention there is provided a wearable apparatus capable of altering the heart rate or other physiological parameter of a user as defined in claim 1. Such other parameters include, for example, breathing. The apparatus may also be useful in facilitating the alteration of other parameters, for example physical parameters such as cadence or stride.

Embodiments of the present invention provide a new method of achieving an alteration in a physiological parameter such as heart rate or breathing, and additionally or alternatively assisting in achieving an alteration in a physical function such as cadence or stride, by providing a rhythmic tactile stimulus through a vibration or movement felt by the user that encourages their heart rate to synch-up or synch-down with the stimulus. That is to say, providing a rhythmic tactile stimulus at a rate that differs from the user's current physiological rate e.g. heart rate can stimulate, encourage or entrain it to match the tempo of the rhythmic tactile stimulus. The tempo of this stimulus can be changed to provide a faster rhythm to raise heart rate and a slower rhythm to reduce heart rate and this can be done at any time during work, rest or play.

In an embodiment, the device is adjustable to change the frequency, tempo, duration and/or intensity of the stimulus delivered to the user and optionally and/or preferably comprises one or more control means for adjusting one or more of the frequency, tempo, duration and/or intensity of the stimulus.

The apparatus may further comprise a device or means to enable tactile and/or gestural interaction by a user with the apparatus. The apparatus may comprise a capacitive or strain sensor configured to enable tactile and/or gestural interaction by a user with the apparatus. The capacitive sensor may be configured to detect movement, e.g. of a finger passed across and/or on it. The apparatus may be configured to be responsive to such tactile or gestural interaction in order to control operation of the apparatus. This advantageously enables a user to easily interact with the apparatus in order to initiate, change and/or cease operation of the apparatus.

In an embodiment, the device is or comprises a motor-driven vibrator configured for delivering the rhythmic tactile stimulus. The device may be or comprise a piezo-electric actuator, a shape changing material, a linear actuator, or a pneumatic or hydraulic actuator configured for delivering the stimulus. The device may be or comprise an electric contact for delivering an electrical pulse that causes a muscle contraction, especially a mild contraction.

As such, the tactile stimulus may be given by a vibration, e.g. provided by a vibration motor or a piezo-electric actuator, or it may be given by a movement by shape changing materials, linear actuators, or pneumatic or hydraulic actuation. The physical stimulus may also be given via an electrical pulse that causes a gentle sensation and muscle contraction.

The device may be configured to provide stimulus in the form of a single repeated beat, or in the form of a double-peaked beat, or in the form of a beat that substantially matches the form of a user's heartbeat. Advantageously, the applicant has found that pulses that are more akin to a user's actual heartbeat work more effectively in heart rate entrainment.

The device may be further configured to provide a further tactile stimulus to a user and/or the apparatus may comprise a second mechanism or device configured to provide said further tactile stimulus to a user, the further tactile stimulus being different in form, frequency, tempo and/or intensity from the rhythmic tactile stimulus, and being deliverable to the user before, with or after the device delivers the rhythmic tactile stimulus. The further tactile stimulus (which may or may not be rhythmic) is preferably an empathic interaction or touch affective sensation, such as a stroking, squeezing, pinching, twisting of the user's skin. The device and/or the second device may comprise actuating means for producing a tactile sensation by applying pressure to the skin of a user directly or by transmission through a non-rigid and/or flexible part of the apparatus. The actuator may be a linear or circular actuator configured for movement across the skin and/or orthogonally thereto for intermittent contact with the skin. In one aspect, the apparatus may comprise a device as described above but configured only to provide the empathic tactile stimulus, i.e. without the rhythmic tactile stimulus.

Embodiments of the invention therefore enable the provision of one, two, or even more tactile sensations, which may be the same, similar or different. The apparatus may be configured to provide the tactile sensations together or separated in time e.g. one after another. The two or more tactile sensations may have different tempos, frequencies, durations, intensities etc. chosen according to the user's wants or needs. In an embodiment, the same device and possibly the same motor/vibration element is used to provide the two or more different tactile stimuli, but this need not be the case.

The device may be worn on the body in order to transmit the tactile stimulus to the user and so may be in the form of a strap or band to be placed around a limb, or as a sticker or adherent pad to be adhered to the skin. It may also be attached to other worn items such as clothes, jewellery or accessories, or in the form of a holder or pouch in an item of clothing or in the form of a piece of jewellery or in the form of an accessory, e.g. a belt, a child's toy or blanket, or in an item of bedding, e.g. a bed, mattress, pillow or duvet.

There may also be further elements of stimulus such as visual or audio cues such as a visual and/or audio output that emits light in synchrony with the stimulus. The visual stimuli could be, for example, in the form of visible moving parts, lights or screens. The audio stimuli could be, for example, in the form of audible mechanisms or sounds from a speaker. In an embodiment, the device comprises a transparent portion to enable a user to see said visual output.

Preferably, the device is or comprises a rigid portion to facilitate transmission of the rhythmic tactile stimulus to the user's skin.

The apparatus may further comprise a data input and/or output to enable the device to connect wirelessly or via a wire, to an external controller or monitor, e.g. a computer or a mobile phone, in order to alter the settings for the different stimuli, e.g. the frequency and/or intensity of the stimulus. A heart rate monitor and optionally also a control capable of altering the stimuli rhythm in response to the heart rate monitored may be provided. The heart rate monitor may be operable to monitor the user's heart rate either in real-time or "offline" to record a user's resting or previous heart rate for later use.

In an embodiment, the apparatus and/or device is further configured to play a user's heart beat back to them via tactile, audio or visual means and, optionally or preferably wherein the playback provides said rhythmic tactile stimulus. Rather than providing for heart rate entrainment, playback of the user's heart beat acts to provide interoceptive awareness biofeedback. This also advantageously provides for increasing the empathic connection between the user and the apparatus. Improved empathic connection may increase the effect of entrainment and thus improve effectiveness of the device. For example, the apparatus/device could feedback to the user for a short period of time to increase the user's empathic connection with the device, and then the stimulus could be applied or increased/decreased to begin entrainment.

The apparatus may further include a clock to activate to provide the stimulus and/or deactivate the device and stop it applying the stimulus at a pre-set time and wherein the apparatus is optionally operable as an alarm.

The device may include a power source. Preferably, the device is powered by a rechargeable battery and may also have the capability to self-charge using piezo-electric or movement based charging mechanisms.

The intensity of the stimuli will generally be enough for the user to feel but not enough to annoy the user. The intensity of the stimuli may be alterable. It should not be so intense that it takes the heart out of a normal heart rhythm.

According to a second aspect of the present invention, there is provided a system as defined in claim 20. The system may comprise any one or more of the features previously described.

The device may be configured to communicate with a computer or computing device in order to alter the settings for the different stimuli.

The system may further comprise a means for recording a user's desired heart rate preferences as one or more profiles, the system being configured such that a user can access said one or more profiles via the device and/or said external controller or monitor to set the desired tactile stimulus.

In an embodiment, the external controller or monitor may further comprise a clock to activate to provide the stimuli and/or deactivate the device and stop it applying the stimulus at a pre-set time and wherein the apparatus and/or system is optionally operable as an alarm.

The device/apparatus may also be connected to a mobile phone, tablet and/or other computing devices. This could be done through a wire or via a wireless connection using Bluetooth or RFID for example. This could enable the device to be used as a sympathetic alarm clock to aid in sleeping and waking.

The stimulus may be applied by a motor-driven vibrator, a piezo-electric actuator, a shape changing material, a linear actuator, or a pneumatic or hydraulic actuator. Delivering the stimulus may comprise delivering an electrical pulse that causes a muscle contraction, especially a mild contraction. The electrical pulse may be in the form of a single repeated beat, or in the form of a double-peaked beat, or in the form of a beat that substantially matches the form of a user's heartbeat.

According to a third aspect of the present invention there is provided a method of altering the heart rate of a user as defined in claim 24.

The method may provide for reading the heart rate of the user to then alter the stimuli rhythm continuously and responsively. The method may implement any one or more of the features previously described.

In an embodiment, the method further comprises providing a further tactile stimulus to a user, the further tactile stimulus being different in form, frequency, tempo and/or intensity from the rhythmic tactile stimulus, and being deliverable to the user before, with or after the rhythmic tactile stimulus. The further tactile stimulus may be an empathic interaction such as a stroking, squeezing, pinching, twisting of the user's skin.

The rhythmic tactile stimulus may be delivered to the user by a device that is held against the user by an arrangement that is in the form of a strap or band placed around a limb, or is in the form of an adherent pad or in the form of a holder or pouch in an item of clothing or in the form of a piece of jewellery or in the form of an accessory, e.g. a belt, a child's toy or blanket, or in an item of bedding, e.g. a bed, mattress, pillow or duvet.

The method may further comprise providing a visual or audio output that emits light in synchrony with the rhythmic tactile stimulus.

In an embodiment, the heart rate of the user may be monitored and optionally the rhythmic tactile stimulus may be controlled in response to the heart rate monitor.

The rhythmic tactile stimulus may be provided at a rate that represents the user's desired heart rate, or wherein the rhythmic tactile stimulus is provided at a rate that is slightly less than or greater than the user's current or resting heart rate and, optionally or preferably wherein the rhythmic tactile stimulus is iteratively increased or decreased until a user's desired heart rate is reached.

The method may also comprise playing a user's heart beat back to them via tactile, audio or visual means and, optionally or preferably wherein the playback provides said rhythmic tactile stimulus.

The device may also be used to help calm children and so be integrated in to toys, blankets or chairs. It may also be used to help both children and adults to sleep and so could be employed in beds, mattress, pillows, duvets or other bedding.

In further aspects there is provided an apparatus and/or system for use in altering the heart rate and/or other physiological and/or physical parameters. Such parameters may include, for example, breathing, stride and cadence.

The features described above in connection with aspects and embodiments of the invention may be used separately or in any combination.

BRIEF DESCRIPTION OF THE DRAWINGS

The invention will now be described in more detail by way of example and with reference to the accompanying drawings in which:

FIG. 10b is a schematic flow diagram showing communication between the system components of FIG. 10a;

DETAILED DESCRIPTION OF EMBODIMENTS OF THE INVENTION

Figure 1:
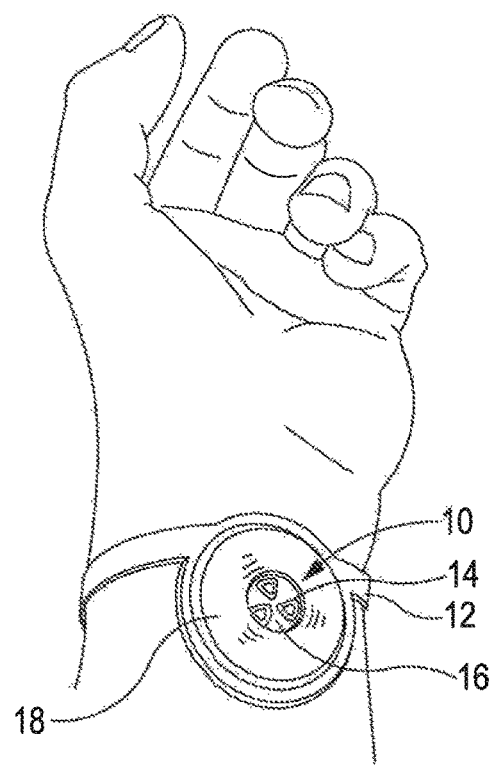
FIG. 1 shows an example of the device worn as a band around the wrist.

FIG. 1 shows a first embodiment of a device 10 configured to alter a user's heart rate. In FIG. 1 the device 10 is strapped around the wrist of a user using a band 12 that may be either hard or soft. The device may, of course, also be placed on or around other parts of the user's body, through the provision of a suitable band, belt, strap etc.

The device 10 is configured to transmit a tactile stimulus to the user. The tactile stimulus may be provided by a vibrating element 14. The vibrating element 14 may be or comprise a vibration motor, a piezo-electric actuator, a shape changing material, linear actuator, pneumatic or hydraulic actuation etc. The physical stimulus may be given via an electrical pulse that causes a gentle sensation and muscle contraction.

The embodiment of FIG. 1 includes a vibration motor 14. The device 10 and/or vibration motor 14 may be at least partially transparent to provide an additional visual stimulus.

That is, the device 10 and/or vibration motor 14 may comprise a transparent portion 16, to enable the user to see the movement of the pulse generator 14 within the device 10. This advantageously provides a visual stimulus in synch with the tactile stimulus. The casing 18 around the vibration motor 14 is preferably rigid, or comprises a rigid portion, to transfer the vibration to the user's skin.

The fact that the motor 14 is visible is important on two levels. Firstly, there is a visual stimulus for the user to further entrain their heart rate in addition to the applied tactile stimulus. Secondly, the visual stimulus is a mechanical motion demonstrating that the wearable device is operational and performing a function. This can act to strengthen trust in the device, as the user can see it is working and what it is doing, and so strengthen the effect.

The device 10 may be provided with one or more control means (not shown). The control means may be or comprise one or more switches or other means for a user to control operation of the device 10. The switches may comprise of sensors of movement, gesture or pressure or simple buttons. The control means may be configured to permit the user of the device 10 to adjust the characteristics of the tactile stimulus (e.g. the intensity, frequency etc.) to suit their requirements and/or comfort levels.

Figure 2:
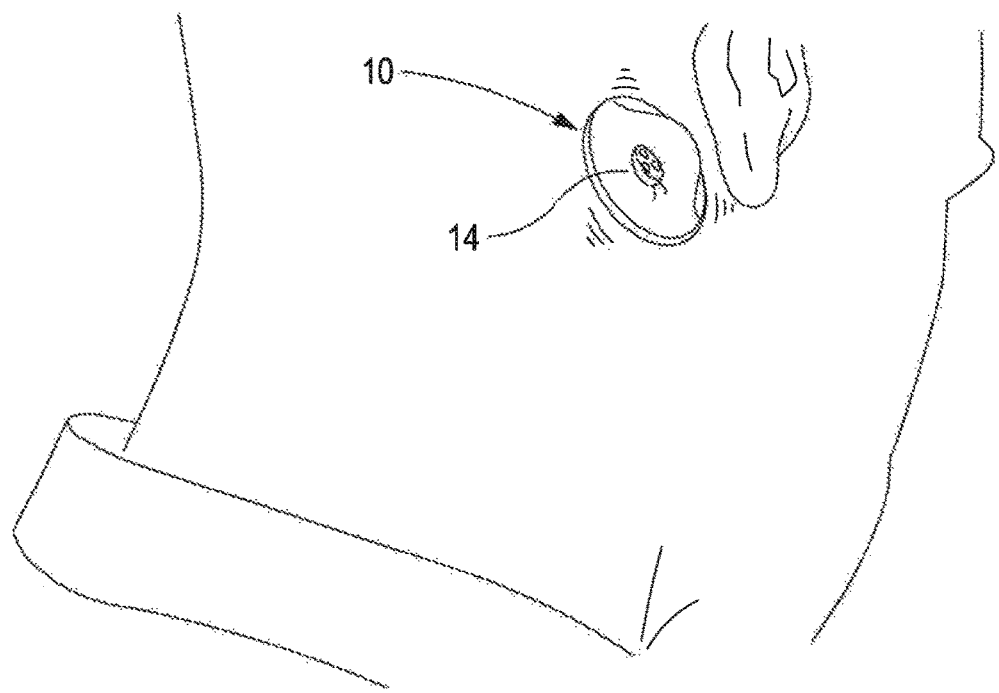
FIG. 2 shows an example of the device as a sticker adhered to the skin.

In FIG. 2, showing an alternative embodiment, the device 10 is adhered directly to the skin to allow for placement anywhere on the body. The vibrating element 14 may be or comprise any of the tactile devices mentioned above, e.g. a piezo-electric actuator, and will be held firmly against the skin to transfer the vibration to the user.

Figure 3:
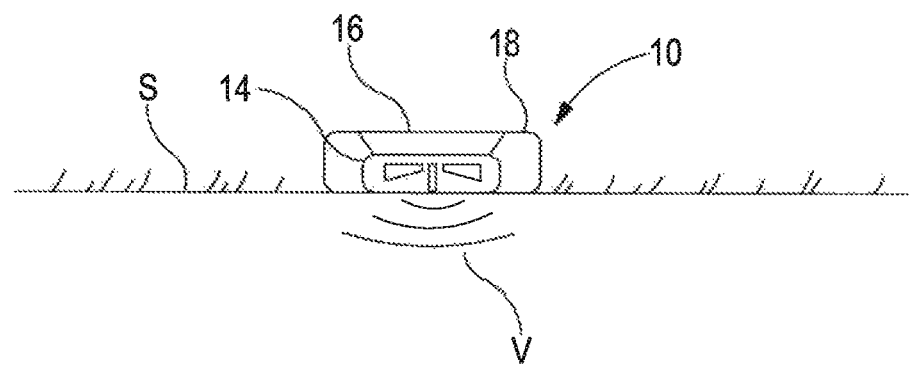
FIG. 3 shows an example of the cross-section of the device in contact with the skin.

In FIG. 3 the cross section shows the vibrating element 14, being held against the skin S, and transferring vibration (V). It is held in a rigid container 18 that transmits vibration (V), with a clear section 16 to see the interior elements 14.

Figure 4:
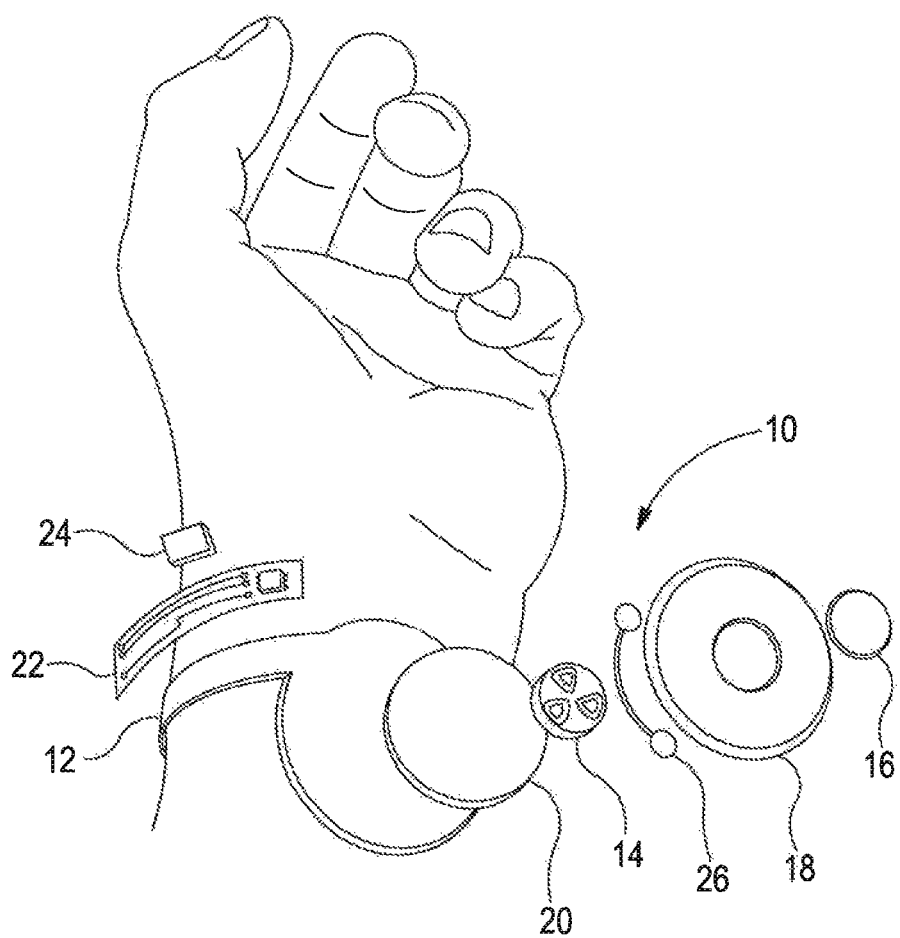
FIG. 4 shows an exploded view of a possible example of elements that would make up the device.

In FIG. 4 the exploded view shows a possible combination of elements comprising of a rechargeable battery 20 that powers the device 10. The device 10 also comprises an open vibration motor 14 that provides the tactile stimulus as a vibration and also a visual stimulus through the motion of the moving parts. A circuit board 22 is operable for controlling the stimulus rates and inputs. A wireless connection in the form of an RFID or Bluetooth chip 24 is provided and which is configured to connect to other devices for the purpose of changing the stimuli and further functionality. For instance, one or more capacitive devices or switches and/or a strain sensor 26 enable tactile and gestural interaction with the device, e.g. in the form of stroking and squeezing, to work as the inputs to change the stimulus tempo. As described above, the apparatus comprises a rigid housing 18 to better transmit the vibration, and a clear viewing window 16 to see the mechanical motion of the open vibration motor 14, all mounted on a silicone wrist band 12. The RFID or Bluetooth chip 24 may be used to calibrate the device 10 and set the parameters of the stimulus. The stimulus is initiated or increase/decreased when the user interacts with the device 10. In the embodiment shown, a capacitive sensor 26 is operable to detect movement such as a user, for example, stroking or squeezing the device 10. The type and intensity of the interaction sensed by the sensor 26 determines what stimulus is applied. In a simple embodiment, if the sensor 26 senses a rapid movement e.g. squeezing this might correspond to a pre-set high-rate stimulus; if the sensor 26 senses a slow movement this might correspond to a pre-set low-rate stimulus. In another embodiment, the intensity of the interaction might also determine the intensity of the stimulus applied.

Generally speaking, for the embodiments of FIGS. 1 to 4, whether the device is worn by the user on a band or suchlike or directly adhered to the skin, the principle of operation is the same and the tactile and/or visual stimulus can be provided in the same way. It may be beneficial for at least a part of the device of FIGS. 2 and 3 to be flexible, to facilitate adherence to the skin but, if at least a part is rigid, then this ensures good transfer of the tactile stimulus to the user's skin.

In addition to the tactile stimulus (pulse) described above, the device 10 may be configured to provide an additional tactile stimulus in the form of an "empathic interaction", such as stroking, squeezing, pinching, twisting the user's skin. FIGS. 5-8 show alternative mechanisms that could be used to provide such a stimulus. This will be described in greater detail below but, essentially, such an "affective touch" mechanism can be used to provide a gentle tactile stimulus to a user that mimics the type of stimulus that a user could apply to his own skin. The mechanisms shown in FIGS. 5-8 thus aim to replicate human touch.

In the embodiments of FIGS. 5-8, a motor 14' is provided which may or may not be the same motor 14 as described above. The motor 14' may be provided substantially centrally within the housing 18', but this is not a requirement—it could be offset from the centre. The housing 18' may be the same as housing 18 described above, but need not be. It is clearly convenient for the two stimulus delivering mechanisms to be provided within the same housing and within the same device, but they do not need to be. The two mechanisms could be provided entirely separately, e.g. on different bands/straps 12, or as different housings 18, 18' on the same band 12, or within the same housing 18/18' using either the same motor or different motors 14, 14'. Any and all combinations are envisaged.

Figure 5A:
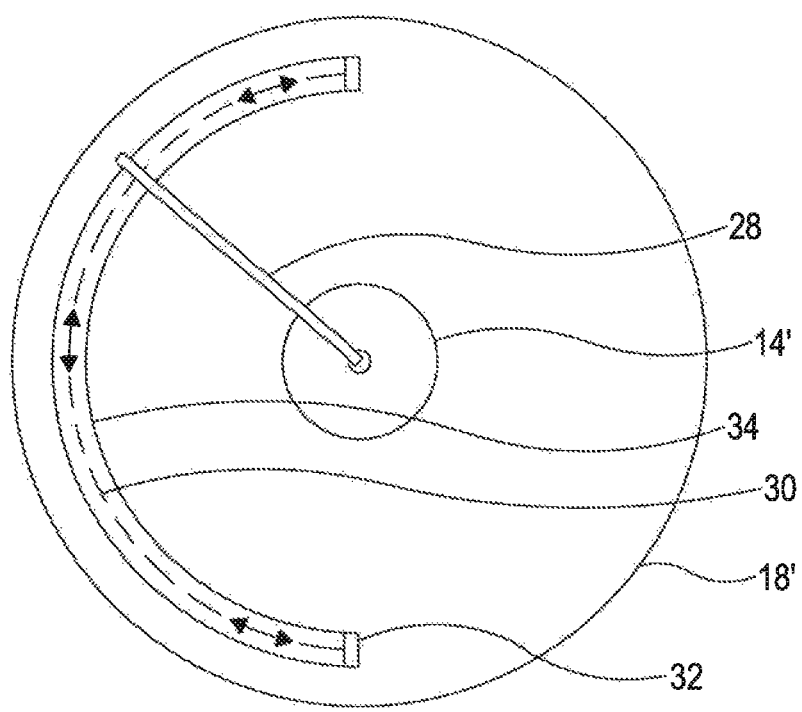
FIGS. 5a and 5b illustrate an affective touch mechanism employed in an embodiment of the present invention in both top plan and side cross sectional views.
Figure 5B:
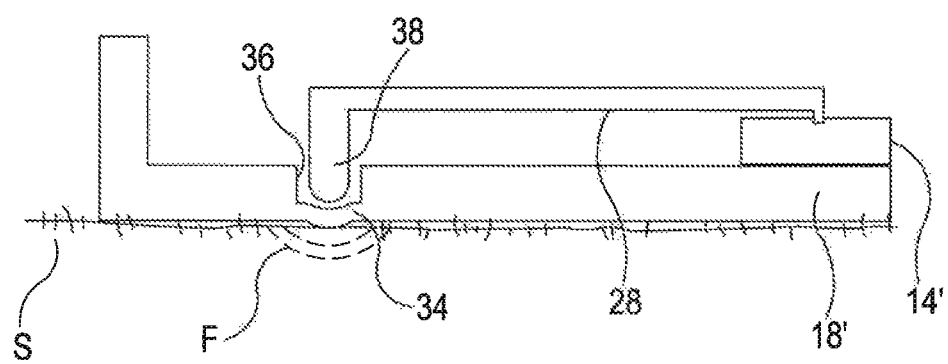

FIGS. 5a and 5b show a first embodiment for implementing an affective touch stimulus using a radial stroking arm. A stroking arm 28 is coupled to the motor 14' and is configured to be driven by rotation of the motor 14' such that the arm 28 describes a circle, or at least a part or an arc thereof, within the housing 18'. In the embodiment shown, the motor 14' is configured to drive the arm 28 backwards and forwards along a substantially semicircular path 30, the ends of which are defined by electronic switches 32. When the arm 28 reaches the limit defined by one of the electronic switches movement of the arm 28 is stopped and reversed so that it travels back along the arc 30 in the opposite direction. The part of the housing 18' that corresponds positionally to the movement arc 30 is or comprises a flexible membrane 34. In the embodiment shown, the housing casing 18' comprises a groove or a portion of reduced thickness 36 in which the free end 38 of the arm 28 can move. The arm 28 is substantially L-shaped to enable such an arrangement. The flexible membrane 34 is thus provided to define a base of the groove 36. The arm 28 is positioned so that the end thereof 38 exerts a force on the membrane 34 and transmits the force F through the flexible membrane onto the user's skin S on the other side thereof. The user can, therefore, feel the pressure exerted and, when the motor 14' is operational, can feel movement of the arm 28 as it describes the arc motion, while the casing 18' remains sealed.

Figure 6A:
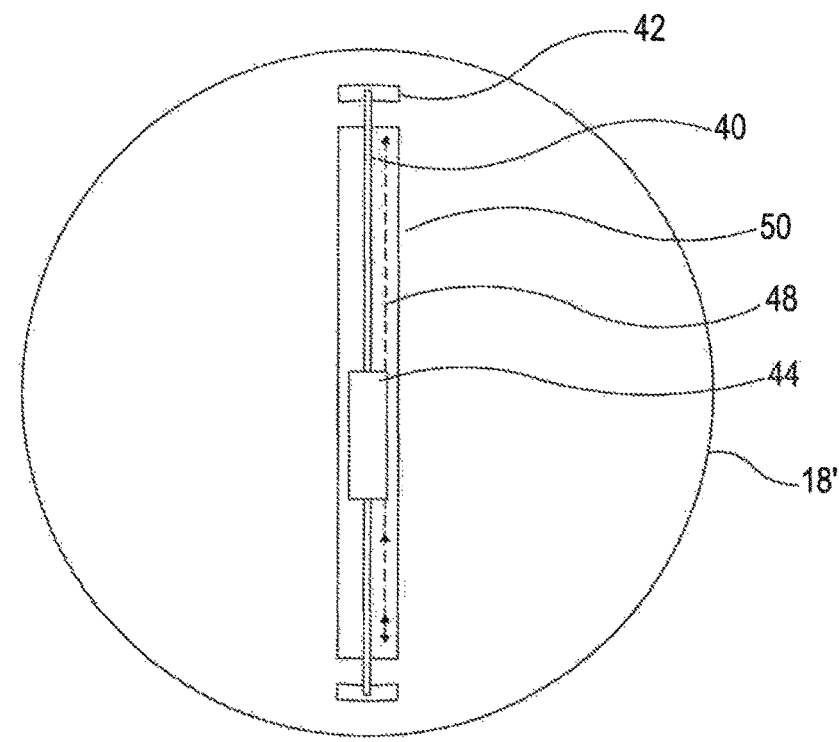
FIGS. 6a, 6b, and 6c illustrate an alternative affective touch mechanism employed in an embodiment of the present invention in both top plan and side cross sectional views.
Figure 6B:
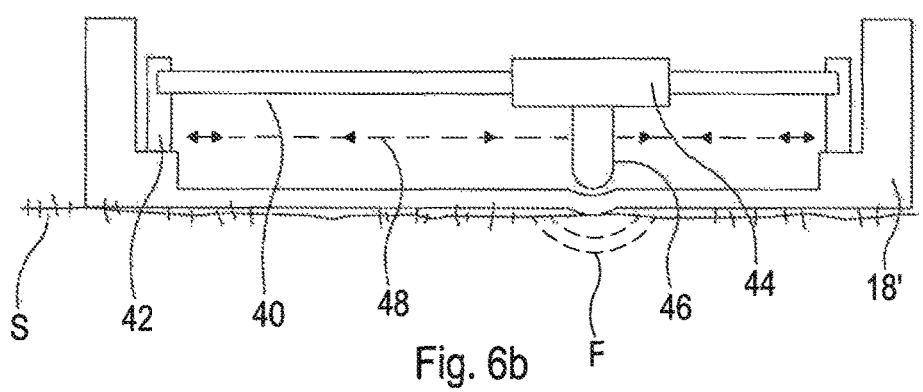

FIGS. 6a and 6b show a second embodiment for implementing an affective touch stimulus using a linear stroking arm. A bar 40 is supported within housing 18' by holders or supports 42. Alternatively, a unitary support may be provided. A linear actuator 44 is coupled to the bar 40 and is moveable linearly along the length of the bar 40. A protrusion 46 is also attached to the linear actuator 44 and is linearly moveable therewith to define a movement path 48. As for the embodiment of FIGS. 5a and 5b, the part of the housing 18' that corresponds positionally to the movement path 48 is or comprises a flexible membrane 34. The housing casing 18' comprises a portion of flexible membrane 50. The protrusion 48 is positioned so that the end thereof 38 exerts a force on the membrane 50 and transmits the force F through the flexible membrane 50 onto the user's skin S on the other side thereof. The user can, therefore, feel the pressure exerted and, when the motor 14' is operational, can feel movement of the protrusion 50 as it traverses the linear path, while the casing 18' remains sealed.

Figure 6C:
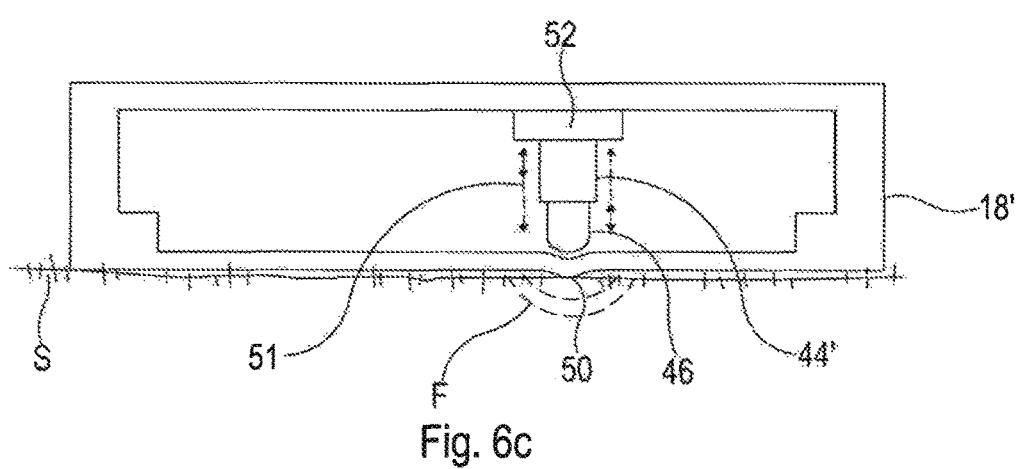

FIG. 6c shows a further alternative embodiment, which may be employed with the arrangement of FIGS. 6a and 6b or separately, whereby the protrusion 46 is mounted with respect to the linear actuator 44' to provide for a transverse motion 51 with respect thereto, i.e. vertically up and down as shown in FIG. 6c. In the embodiment shown, the linear actuator 44' is mounted to the interior of the housing 18' on an optional support 52. The protrusion 46 is fixed to the linear actuator 44' and moveable transversely therewith so as to exert a force upon a portion of flexible membrane 50 provided as part of the housing 18'. The force F is transferred to the user's skin S. The resulting pressure felt by the user is that of an intermittent pressing on the skin, while the casing 18' remains sealed. This could be used alone or in combination with the linear stroking mechanism of the embodiment of FIGS. 6a and 6b.

Figure 7A:
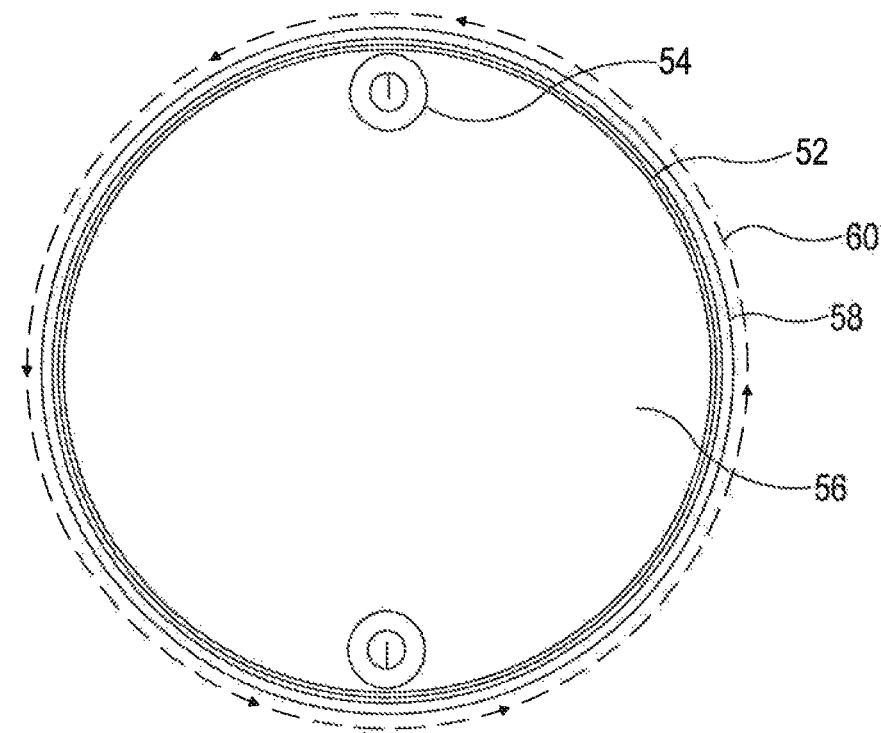
FIGS. 7a and 7b illustrate an affective touch mechanism employed in another embodiment of the present invention in both top plan and side cross sectional views.
Figure 7B:
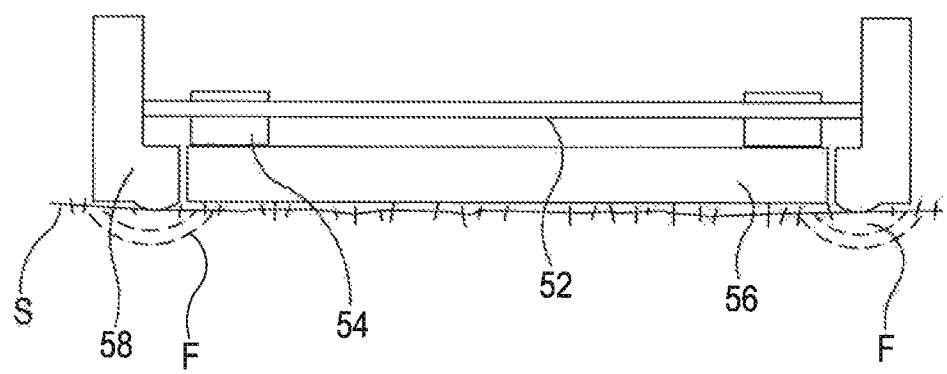

FIGS. 7a and 7b show another embodiment for implementing an affective touch stimulus using a circular pulley. A pulley band 52 is mounted around a plurality (e.g. two) pulley wheels 54. The pulley wheels 54 are fixed to a static (preferably rigid) base 56 that is fixed to or forms part of housing 18'. The pulley band 52 can rotate around the pulley wheels 56. An outer rotating bevel 58 is fixedly attached to the pulley band 52 and is moveable therewith. The bevel 58 is configured to contact the user's skin S. The bevel may be configured to extend beyond the surface of the static base 56 that is also in contact with the user's skin S so as to make a higher degree of contact therewith. Movement of the pulley band 52, and thus of the bevel 58, describes a circular path 60 and causes a force F to be exerted directly onto a user's skin along said path 60.

Figure 8A:
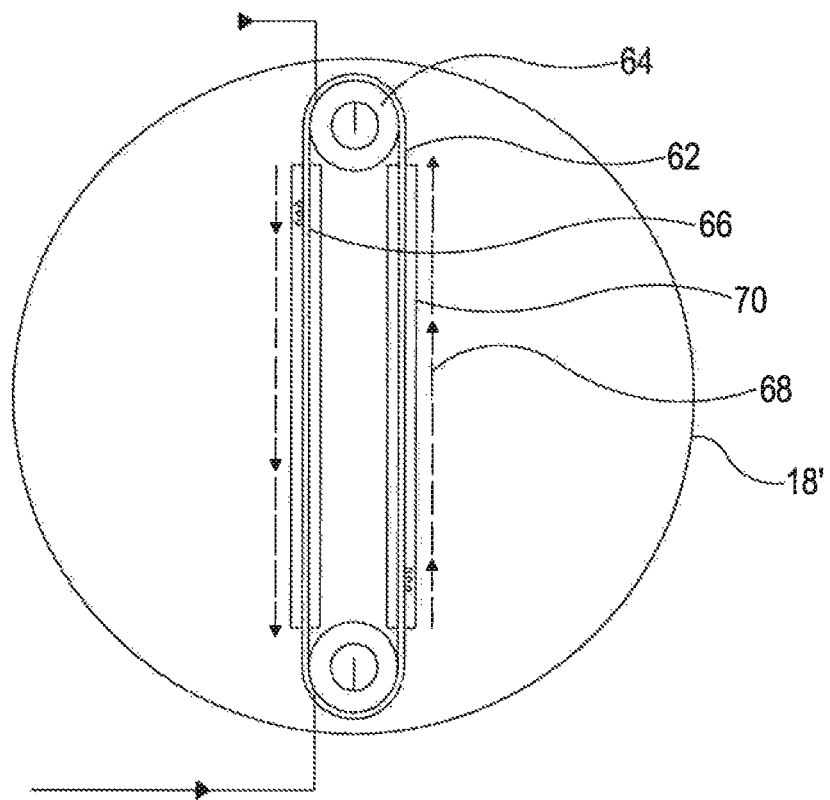
FIGS. 8a and 8b illustrate an affective touch mechanism employed in yet another embodiment of the present invention in both top plan and side cross sectional views.
Figure 8B:
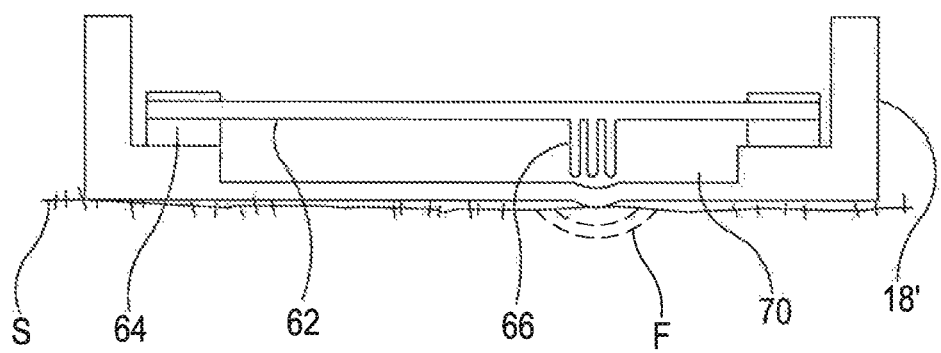

Finally, FIGS. 8a and 8b show another embodiment for implementing an affective touch stimulus using a linear pulley. A pulley band 62 is mounted around a plurality (e.g. two) pulley wheels 64. The pulley wheels 64 are fixed to and within the housing 18'. The pulley band 62 can rotate around the pulley wheels 56. One or more protrusions or tactile points 66 are fixed to the pulley band 62 and depend therefrom. Movement of the pulley band 62 describes an elliptical path 68. The surface of the housing 18' in contact with the user's skin comprises a portion of flexible membrane 70. The protrusions 66 are arranged so that they press onto the flexible membrane 70. Movement of the pulley band 62 thus causes a force F to be exerted onto the flexible membrane 70 and to be transmitted to the user's skin S along said path 68, while the casing 18' remains sealed.

Use of the device 10 will now be described. Generally the user's heart will respond to the applied stimulus and tend towards a heart rate corresponding to the frequency of the applied stimulus. Therefore, in order to increase the heart rate, a stimulus is applied to the user's skin with a frequency greater than the user's present heart rate; similarly, the heart rate can be slowed by applying the stimulus at a frequency less than user's present heart rate.

Several modes of operation are possible to achieve the desired heart rate. For example, in order to increase a user's heart rate, it is possible simply to set the desired heart rate on the device and allow the actual heart to move towards the set stimulus frequency. Alternatively, the user's heart rate could be monitored and the stimulus applied at a frequency slightly greater, e.g. 5 times/minute greater, than the actual heart rate until the desired heart rate is achieved. Similar regimes could be applied to slow the user's heart rate. That is, the user's heart rate could be monitored and the stimulus applied at a frequency slightly lower, e.g. 5 times/minute lower, than the actual heart rate until the desired heart rate is achieved. In another embodiment, the user's heart rate could be monitored and the stimulus applied as described to increase/decrease the user's heart rate, but with the frequency and/or intensity of the stimulus being altered iteratively until the desired heart rate is reached. I.e. the user's heart rate is raised/lowered gradually, step-by-step. The iterations may be equal in terms of the change of frequency/intensity, or unequal/variable, depending on the desired result. For example, if a user is exercising, they may wish to warm up first and so have a slow increase in heart rate, and then have a higher intensity workout and so the stimulus pulse could jump up to a higher level.

Figure 9:
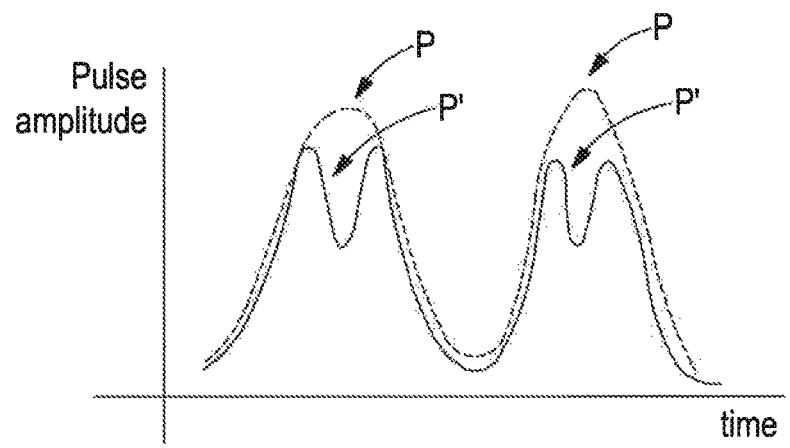
FIG. 9 shows an exemplary pulse waveform provided in an embodiment of the present invention.

FIG. 9 shows, in dashed lines, an exemplary pulse P that may be provided by the vibration element 14 of embodiments of the present invention. This represents a regular pulse P, provided to a user over time, having an amplitude chosen to produce a tactile stimulus of a desired intensity. In an alternative embodiment, the vibration or pulse provided by the vibration element 14 is a "double beat" pulse P', denoted by the unbroken line. Here, each pulse P' is a double-peaked pulse, each of which provides a desired intensity. The intensity/amplitude of the pulses P, P' does not have to sit within the same envelope—FIG. 9 is by way of example only. The frequency and intensity of each pulse P, P' can be chosen to meet a user's requirements. A double pulse P' is closer to a person's actual heartbeat, since the two sides of a person's heart beat separately, and it is therefore believed that a user will have more affinity with a device configured to operate in this way and thus that the device will be more effective. Employing a double-beat pulse that is closer to a user's heart rate than a single pulse is believed to improve performance of the device. In a further embodiment, a level of variability could be introduced in the double beat pattern to more closely simulate a healthy heart beat.

Figure 10A:
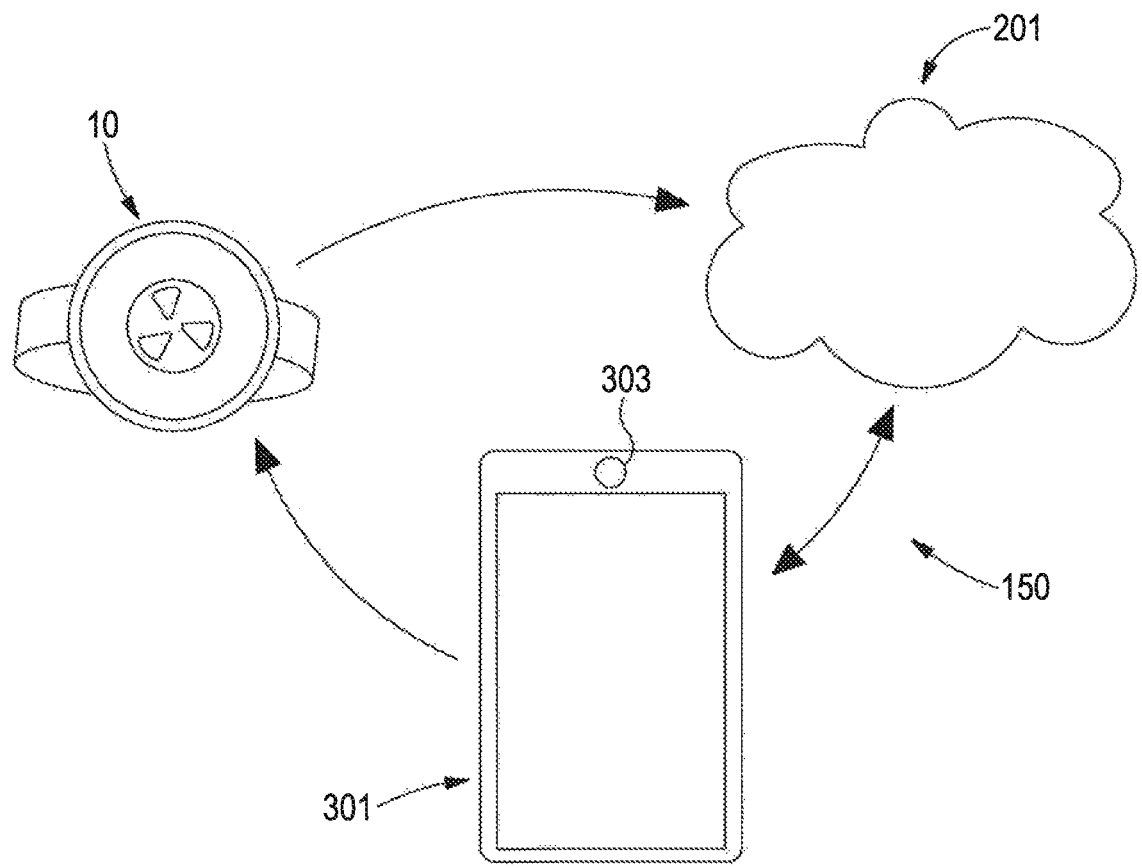
FIG. 10a is a schematic view of a system incorporating the device of FIG. 1.

FIG. 10a is a simple schematic of how the device 10 can be used in a communications system 150. As mentioned above, the device 10 may communicate with a mobile phone, tablet and/or other computing device 301. The computing device 301 is preferably configured to transmit information to the wearable device 10, but may also/instead be configured to receive information therefrom. The wearable device 10 is preferably configured to transmit information to a cloud network 201 and/or may be configured to receive information therefrom. It is, however, desirable to keep the size of the device 10 small, for reasons of fashion, comfort and/or useability. A further determinative factor in the size of the device 10 is the battery requirement. To minimise the size of the device 10, therefore, it is desirable to provide some or most of the computing/processing components and features in the computing device 301 rather than in the wearable device 10. The computing device 301 is preferably configured for two-way communication with the cloud 201, but the communication may instead be one-way.

Figure 10B:
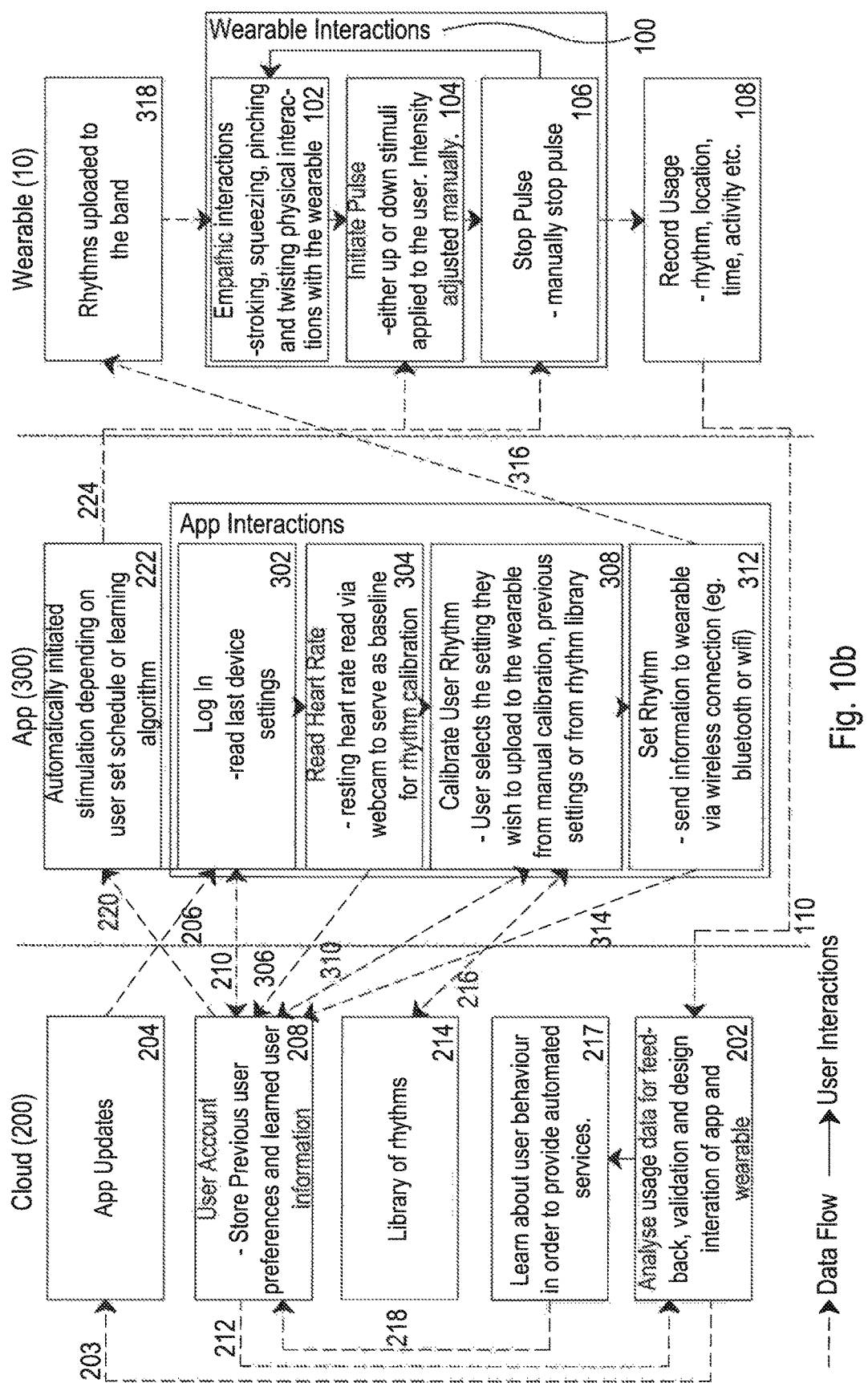

FIG. 10b is a flow chart depicting a system and interaction between the device 10, the mobile/computing device 301 and the cloud 201. Unbroken line arrows represent interactions between a user and the device 10. Broken line arrows represent data flows within and between the different system components. Generally speaking, the steps fall into three categories: processes of and/or interactions 100 with 100 the wearable device 10; processes 200 carried out in the cloud storage 201; and processes 300 carried out by software or an application on a connected computing device 301, such as a mobile phone, tablet etc. Communications between the device 10, the computing device 301 and/or the cloud 201 may be achieved via a wired connection, but preferably by a wireless connection such as Bluetooth or WiFi.

Firstly, the processes 100 carried out by or with the device 10 are illustrated on the right hand side. In step 102, a first tactile stimulus is given to a wearer of the device 10. This tactile stimulus may be an "empathic interaction", such as stroking, squeezing, pinching, twisting the user's skin. This is based on techniques that people have previously used, e.g. stroking the inside of their wrist, to produce a calming effect. Embodiments of the invention thus build on the empathic mechanisms that humans have learnt in order to calm and stimulate themselves.

In an embodiment, the first tactile stimulus is provided to the user's skin using one of the arrangements previously described with respect to FIGS. 5-8. The capacitive sensor 26 is configured to detect movement as previously described, and/or the circuit board 22 may comprise a sensor to detect the movement. The circuit board 22 may also comprise a processor for analysing the detected movement and extrapolating a tempo therefrom, e.g. equal to the frequency at which the user is applying the first tactile stimulus, and to provide this as an input to set the frequency of the second tactile stimulus. The intensity and/or frequency of this component may be pre-set or determinable by the user. For example, there may be pre-set 'calm' and 'energetic' settings at low and high heart rates respectively. In either case, embodiments of the invention thus employ empathic techniques in a technical way, to boost the effect of the entrainment.

Experiments have been conducted by the applicant as to the power of affective touch, and to investigate whether that particular sensation, which is used for bonding and communication (particularly of emotion), can be used to create a feeling of body-ownership (that it is part of their body) between people and non-human looking objects. The results show that it can, to a degree, and so embodiments of the present invention aim to create the same effect in doppel.

By applying the stimulus through a soft 'stroking' mechanism (especially for the calming) it could be possible to amplify the effect of entrainment by making the object 'feel as if it is a part of their body'. This is important because an effect that embodiments of the invention aim to create, at least in part, is psychological, and so the whole user experience, and a form of empathy with the object, will increase its effect.

In step 104, a second tactile stimulus is given to the user. This second tactile stimulus is a pulse of a predetermined frequency and intensity, as discussed above. The user can control the intensity and/or frequency manually using the control means. The user can also operate the control means to stop the pulse, in step 106.

Embodiments of the invention thus provide for application of first and second tactile sensations to a user's skin. The first tactile sensation is an empathic, affective touch sensation and is provided from the arm 28, 38, protrusion 46, bevel 58 and/or protrusions 66 described with respect to FIGS. 5-8. The second tactile sensation is aimed at altering the user's heart rate and is provided by the pulse generator or vibration motor 14 of FIGS. 1-4. Additional tactile sensations could be provided by these or additional components arranged to provide the same, similar or different tactile sensations as required. The characteristics (e.g. frequency/tempo, intensity, duration etc.) of each sensation provided may be tailored for the required use. For example, a user may utilise the first tactile sensation in order to alert/train his body to the fact that he is about to initiate heart rate entrainment using the second tactile sensation (which may be set to provide stronger stimuli to the user), or a user may use the first tactile sensation to provide a gentle stimulus to ease his heart rate towards the starting stimulus provided by the second tactile stimulus. Furthermore, since the first and second tactile stimuli can be different, a user can pick and choose a programme of stimuli that he desires for a particular occasion, providing much greater choice and freedom than has previously been possible.

The circuit board 22 of the device 10 records information such as usage of the device 10, the rhythm of the tactile stimulus used (e.g. single beat, double beat, pace of pulse etc.), the user's location (a GPS element may be included in the device 10 or on a connected device), time (e.g. duration of usage, time of day when used), activity etc. (step 108). In the latter regard, the circuit board 22 may record what activity is being undertaken (which can be determined through means of deduction from location, time etc., through deliberate user input, or from the 'style' of stimulus used e.g. there may be settings for 'sport' and 'sleep'). The device 10 may include one or more activity monitor such as an accelerometer to monitor the number of steps taken, cadence, altitude, speed etc. during an activity or sport, or to detect movement during sleep.

Information recorded by the device 10 in step 108 can be communicated to cloud storage 201 (step 110). In particular, in step 202, the usage data can be analysed for feedback, validation and design iteration of the connected device application and device 10. This information is communicated 203 and used in step 204 to produce application updates dowloadable to the connected device 301 in step 206. The cloud 201 can also be used to store user account details and previous user preferences (208). This information can feed into and the connected device (step 210) and can be updated by the connected device 301 (as will be discussed later).

This information can also be used as an input 212 in the analysis of step 202. The information can also be used by a learning module where, in step 217, the learning module learns about user behaviour in order to provide automated services as is discussed in more detail below. The learning module can pass this information to the user account, in step 218. The cloud 201 can also store 214 a library of rhythms which can feed into/be read from 216 the connected device 301.

As previously mentioned, the device 10 is also configured for wired or wireless communication with the computing device 301. The computing device 301 can run software (an application) that provides the user with greater control over the device 10 and/or with additional functionality. At step 302, the user can log in to a personal account/profile. The application can access the user's preferred and/or last settings for the device 10 through communication with the cloud 201 (step 210). In step 304, the connected device 301 reads the user's current or resting heart rate. This can be achieved by using a web cam 303 on the connected device 301 and setting the initial stimulus therefrom. This can be achieved by measuring the colour change in the user's skin due to blood flush using known techniques. The connected device 301 can convey information relating to the user's resting heart rate to the cloud in step 306. In step 308, the connected device 301 performs a calibration. Here, the user selects the settings they wish to upload to the device 10 from manual calibration, previous settings (reading from the cloud in step 310) or from the rhythm library (step 216). Preferences determined at this step can also be stored in the cloud 201 for future use (step 310). In step 312, the rhythm is set and information is sent to the cloud storage 201 in step 314, saving the preferences/information for potential future use, and information is sent to the device 10. In step 318, the desired rhythm(s) is(are) uploaded to the device 10.

The user account, which stores previous user preferences and learned user information, can pass information (step 220) to an automatically initiated simulation depending on a user set schedule or learning algorithm (222). This is linked/feeds in 224 to steps 104 and 106 which relate to initiating and stopping the second tactile sensation.

Embodiments of the invention therefore provide a system and device that can learn about a user's needs and respond to them. The system may include a learning algorithm to process the collected data (user preferences from step 208 and/or usage date from step 108, for example) and self-calibrate the stimulus. The learning algorithm may also process collected data from other sources, for example gps data, movement sensor data, schedule information, social media data etc. For example, the gps pattern of the user may infer that they are jet lagged. A sentiment analysis of the user's emails or tweets may suggest they are stressed or depressed. Analysis of their calendar may indicate when the user has a stressful meeting or an examination. Historical data may suggest that the user goes to bed at 11 pm but has trouble sleeping (an accelerometer knows they are tossing and turning for too long after they lie down), so the device may start gently calming them at 10:30 pm. Or, the data may indicate that the user likes to go for a run at 8 am and the device can learn such habits and deliver a stimulus in advance at, say 07:50 am, to energise them prior to their exercise. This can be done without the user having to pre-program the device. The historical information may be stored in the device 10, or in the connected device 301 or in cloud storage 201.

In the embodiment described above, the connected device 301 is used to read the heart rate of the user and to alter the settings on the wearable device 10. This reading is not done in real-time, and so essentially provides a calibration. The settings for the rhythms are then uploaded to the wearable device 10 and can be activated at will using physical interactions on the band independently of the connected device 301. Advantageously, the wearable device 10 can be used independently of the smart device 301, so users do not have to be ever more connected. Another advantage is that previous preferences can be saved for different 'profiles' for different applications of use. For instance, higher tempo levels can be saved for a 'running and a warm down' setting, than for a 'working late and winding down' setting.

In an alternative embodiment, the user's heart rate could be monitored in real-time. A process by which the heart rate of the user is read live by the wearable device 10 could be incorporated to allow for reactive changes in the stimulus. The heart rate could be measured using various techniques such as a measurement of colour change of the skin, change of light passing through the skin, electrocardiogram (ecg), movement of skin surface caused by pulse. This could be used to cause a feedback loop to change the heart rate of the user gradually by moving it one beat at a time.

In an embodiment, the device 10 is operable to 'play' the user's heart rate back to them. This has two purposes. Firstly, it can be used as a 'bio-feedback' device so that the user can improve their knowledge of their state and learn how to control it through breathing, meditation and/or other techniques. For example, the device 10 may play back a user's heart rate to him for, e.g. 5 minutes, increasing empathic connection with the doppel, and then the physiologically altering stimulus may be applied. Secondly, the applicant has conducted experiments to demonstrate that people empathise with inanimate objects that have similar biorhythms—as they do with people who have similar biorhythms. Heart rate entrainment has been observed between people—their heart rates synch with one another. Embodiments of the present invention aim to achieve the same effect but with an inanimate object rather than a person. This is a two-way process. If the device shows a user his heart rate, he will empathise with it; and if he empathises with the device, he is more likely to change his heart beat to match the beat of the device if it differs from his own. So, by doppel matching the heart rate of the user with the device stimulus, it will increase the empathy between the person and the object and again potentially amplify the entrainment effect.

An important feature of embodiments of the invention is the ability for the user to be able to alter the pulse rate both through the wearable device 10 (via the controls provided thereon) and/or the computing device 301. This both provides the user with superior control over operation of the device, and enables the user to adopt a preference for how he controls operation of the device 10, which has been found to be an important psychological mechanism. To this end, the user is able to alter the rate of the pulse both through the connected device 301 and on the wearable device 10 itself. This can be achieved, for example, by changing a code on the device 10 or changing an analogue signal within the device 10. This change will control the stimulus via a pulse width modulation (PWM) signal. A signal can alter a variable within the code (e.g. the heart rate, by increasing the delay between pulses) to change the current or voltage output to the actuator. Alternatively, this can be achieved through physical alteration of the circuit. For example, if a potentiometer or variable resistor is used, the current/voltage can be increased or decreased to increase or decrease the intensity. Alternatively, manually altering the current/voltage through part of the circuit can be used as a signal to instigate a change by means of circuit logic. The intensity of the pulse can also be altered either through a physical or electrical element on the wearable device 10 or through the connected device 301. This can be controlled through a variable resistor that is manipulated physically through the use of a linear or circular actuator in the device 10. This may be achieved by providing a linear mechanism or a circular bevel around the outer edge of the apparatus, similar to that provided on watches. The user can twist the bevel and, through a linkage twist a variable resistor, which will then alter the voltage/current. Alternatively, a digital or analogue signal can instruct the alteration in resistance. This could be delivered via the connected device 301 or through the use of buttons/switches/sliders/dials or other physical control on the wearable device 10.

The device and method of the present invention can be used in therapeutic or non-therapeutic applications to speed-up or slow down the heart rate. One may want to speed up the heart rate to increase vitality, e.g. in the morning to get the user going instead of a strong cup of coffee or when feeling lethargic or before exercise. One may want to slow down the heart rate in order to calm down and relax, e.g. after exercise or after a stressful workday or as an aid to sleep. In particular, the device 10 can be used to raise a user's level of alertness or to make them feel more relaxed.

Figure 11:
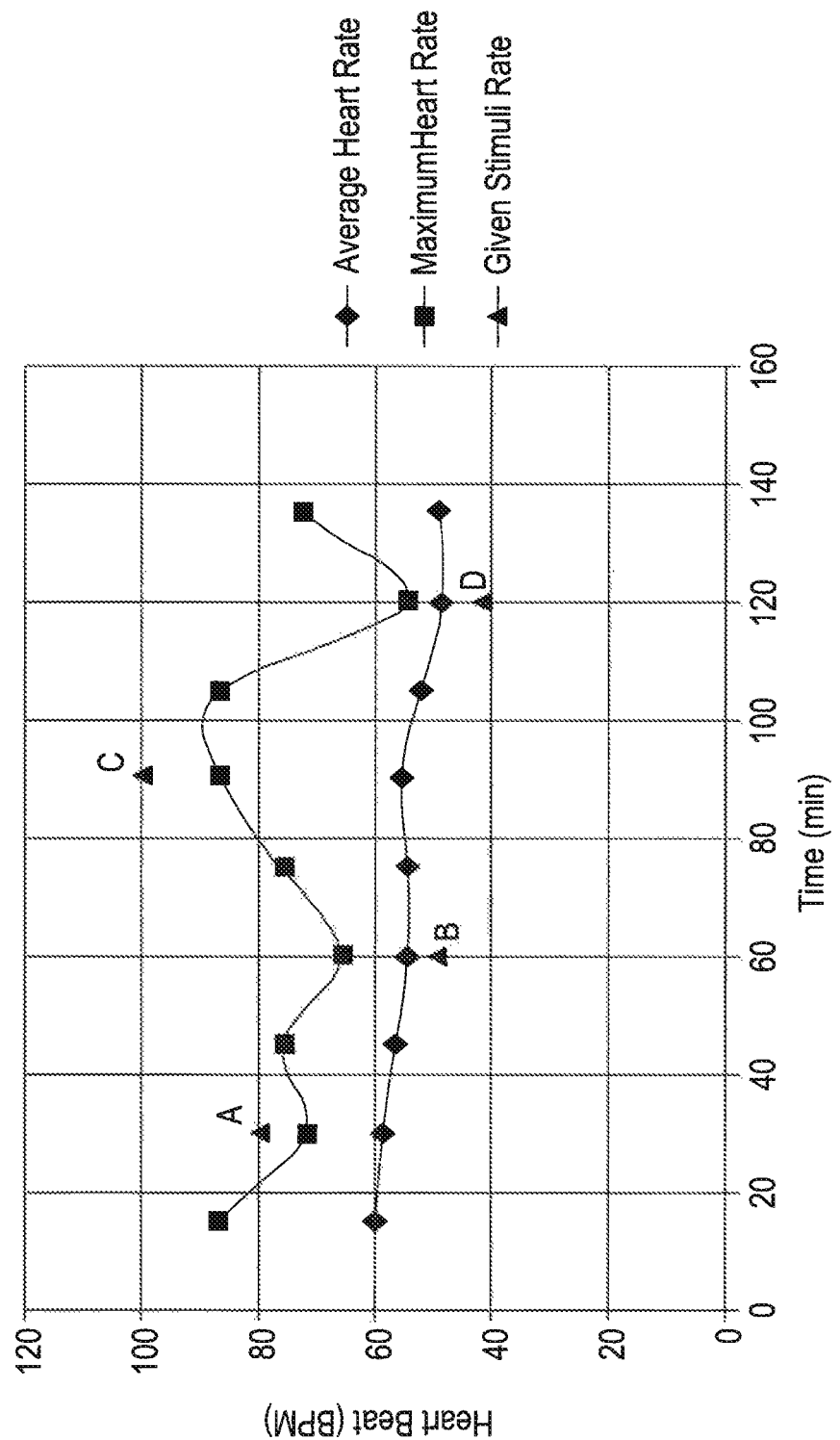
FIG. 11 shows experimental results obtained by implementing an embodiment of the present invention.
Figure 12:
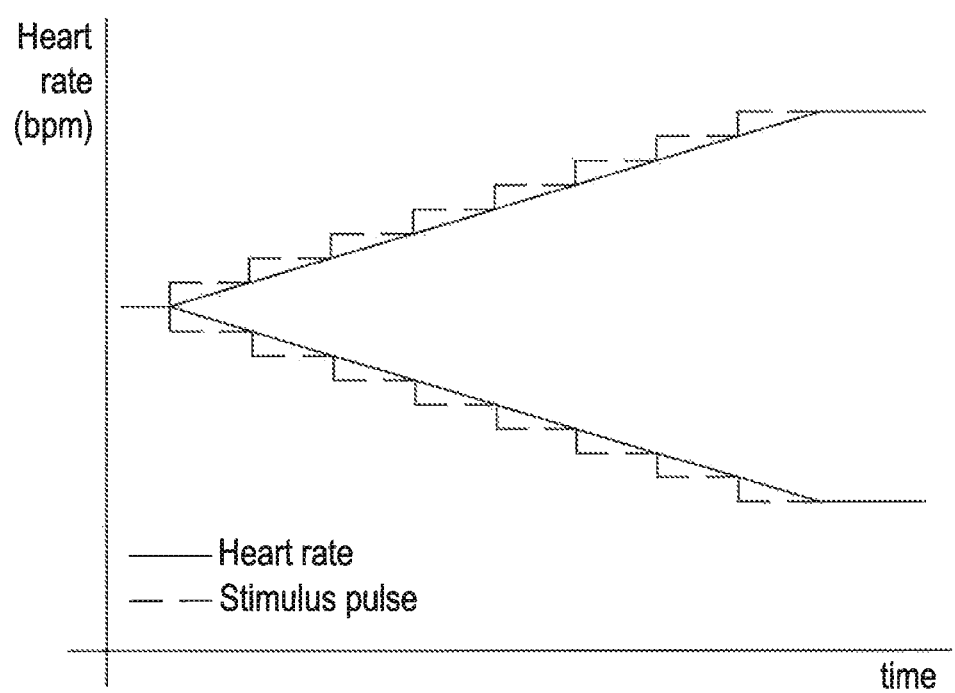
FIG. 12 is a schematic representation of the effect changing the stimulus pulse has on a user's heart rate.

FIG. 11 shows a graph showing a user's heart rate in beats per minute (bpm) against time in minutes. The points depicted by the triangles show when a stimulus was applied by the device 10. Points A and C represent stimuli at relatively high pulse rates, and points B and D represent stimuli provided at relatively low pulse rates. The data represented by diamonds show the user's average measured heart rate and the data represented by squares show the user's maximum measured heart rate. It can clearly be seen that providing a stimulus at a high pulse rate causes the maximum heart rate to increase, and providing a stimulus at a lower pulse rate causes the maximum heart rate to decrease. The device 10 is therefore effective at increasing and decreasing a user's heart beat on demand. FIG. 12 is a schematic representation of how changing the frequency of the stimulus pulse iteratively can cause a cumulative effect to increase or decrease a user's heart rate.

Of a sample of 15 people who tested using the device, 100% of the sample group confirmed that they could feel a stimulus being applied when the device 10 was operational and producing a stimulus. Of these 15 people, 80% classed the experience as good, with just 20% of people considering using the device as a bad experience. Of those that had a positive experience, users found application of a low pulse rate to be pleasant, relaxing comfortable and/or calming. Users found application of a high pulse rate to make them feel energetic, alive and/or awake, and/or produce a fun effect.

The stimulus, as noted above, could react to the readings given by various bio-monitoring inputs. This may not just be for a step-up/step-down loop but it could also instigate the stimulus. By reacting to a signal, for instance increased heart rate, operation of the wearable device 10 could be instigated without the user having to interact with it. By measuring different inputs the wearable device 10 could, for instance, determine stress levels, levels of arousal or excitement. The inputs could be heart rate, skin conductance, breathing rate, pupil dilation, brain activity, temperature etc. Once these reach a threshold level (either greater or lesser) the stimulus would be activated until the input had returned past the threshold. This would be especially effective for dealing with stress, anxiety, depression and other psychological problems.

In an alternative embodiment the wearable device 10 could be linked to a clock and/or an alarm, either through connection to another device that measures time, such as the connected device or a separate timing device, or within the device 10 itself. It could then be used to help the user get to sleep more easily and wake up more effectively. To help the user get to sleep the device 10 would gradually decrease the stimulus rate and intensity from a set point down to another set point over a specified period of time. To help the user wake up the device 10 would start at a specified time before the user wants to wake up. It would gradually increase the rate and intensity of the stimulus from a set point up to another set point over a specified period of time. This could also be linked with monitoring of biorhythms and movement to detect when the user is in deep or light sleep. This could be used to optimise the application of the waking or soporific stimuli.

A clear application for the use of a sleep aid/alarm clock would be in helping people to overcome the effects of jet-lag. For this a programmable schedule over a number of days could be implemented to help the transition from one time zone to another. The waking stimulus could be set to turn on when it is waking hours in the current time-zone, but sleeping hours according to the user's body clock. This would shift as the user becomes more acclimatised to the current time-zone. Vice versa, the soporific stimulus could be applied when the user should be feeling sleepy and in bed but their internal body clock is telling them to be awake. Again this would shift as their body clock moved towards the new time-zone.

As a natural intervention, which is seen very strongly between mother and child, entrainment is a safe way to encourage children to sleep and concentrate. Metronomes are used for concentration and productivity in therapies for ADHD and children experience the same reaction to music as adults. For this a smaller wearable device would be required that needs to be softer and have fewer interactions. When the child is young it is likely that nearly all interactions would be removed from the wearable device and it would be completely controlled via the parent's connected device 301.

Entrainment can occur between our internal biological rhythms—heart rate, breathing etc., and other stimuli. It can also occur between our external rhythms such as step rate when walking alongside another person. By providing a stimulus input beat this can be used in a sporting context, particularly for training but possibly as a performance aid in competition if permitted.

Small audio metronomes already exist on the market and are used for this, although, they can be annoying, distracting and impractical. Headphones prevent the ability of a user to pay attention to their surroundings, be that for pleasure or safety on the street. They also do not work for a water-based activity. By moving the computing in to a connected device 301 but with the wearable device 10 remaining stand-alone, it is possible to create a smaller, lighter wearable device that does not require the carrying of a phone or other smart device 301. This frees up space within the device for a battery of better capacity, providing superior battery life. The resulting device is more robust, and relatively inexpensive. Preferably, the device is waterproof (to permit use in water sports etc.). Preferably, a training schedule is programmable so interval training, warm ups and cool downs can be planned in advance (to again avoid the need for the device to contain processing means to do this, and avoid the user needing to carry the connected device 301). The training schedule(s) can be uploaded to the wearable device 10. In an embodiment, there is also be a 'get-going' stimulus that is initiated before the start of exercising if the user is feeling lethargic and wants to go but is not in the mood. This can be programmed to start at a specified time before the user wants to go. As with reactive monitoring for heart rate entrainment, this could also be used for cadence entrainment. Cadence is the rate of a repetitive motion such as stride frequency, the rotation rate (revolutions per minute, for example) of bicycle pedals or the frequency of a stroke during swimming. The user's current cadence can be measured and then the stimulus altered to be slightly higher or lower than that. As the user changes cadence this can then be stepped again, until they reach their target value.

Experiments by the applicant have suggested that the mechanism at work may not necessarily be a simple matter of entrainment but, when a user experiences a tactile stimulus, they actually consider it to be their own heart rate and so their body responds to it as though it were by aligning their actual heart rate with the applied stimulus. As such, the apparatus can be used to "entrain" other physiological and physical parameters with the same effect. For example, applying the stimulus may directly cause an effect on physiological parameters such as a user's heart rate and breathing, and may also help bring physical parameters (such as cadence and stride) to a desired pace. Advantageously embodiments of the invention provide a psychological effect whereby the whole user experience, and empathy with the device, increases its effect.

The invention claimed is:

1. A method for providing a relaxing or stimulating effect on a user, the method comprising:
   physically engaging a device to the user's skin on an inner wrist of the user, wherein a rhythmic tactile stimulus is applied to the inner wrist of the user as a double-peaked pulse beat that substantially matches a form of a human heartbeat; and
   controlling a frequency, tempo, duration and/or intensity of the stimulus so as to provide the stimulus to the inner wrist of the user at a rate that is faster or slower than a current heart rate of the user to thereby provide the relaxing or stimulating effect.

2. A method according to claim 1, wherein the beat is a single beat.

3. A method according to claim 1, wherein the method alters the heart rate and/or one or more other physiological parameters of the user to provide the relaxing or stimulating effect on the user.

4. A method according to claim 1, wherein the stimulus is applied by a motor-driven vibrator, a piezo-electric actuator, a shape changing material, a linear actuator, or a pneumatic or hydraulic actuator.

5. A method according to claim 1, wherein visual or audio output is provided in synchrony with the stimulus.

6. A method according to claim 1, further comprising monitoring the heart rate of the user.

7. A method according to claim 6, wherein a heart rate monitor for performing the monitoring is integrated into the device or separate from the device.

8. A method according to claim 1, wherein the stimulus is provided at a rate that represents a desired heart rate of the user.

9. A method according to claim 1, wherein the stimulus is provided at a rate that is slightly less than or greater than the current heart rate of the user or a resting heart rate of the user.

10. A method according to claim 1, wherein the stimulus is iteratively increased until a desired heart rate of the user is reached.

11. A method according to claim 1, wherein the stimulus is iteratively decreased until a desired heart rate of the user is reached.

12. A method according to claim 6, further comprising controlling the stimulus in response to the monitored heart rate.

13. An apparatus for providing a relaxing or stimulating effect on a user, the apparatus comprising:
   a wearable device configured to engage the user's skin and also configured to provide a rhythmic tactile stimulus to the user as a double-peaked pulse beat that substantially matches a form of a human heartbeat;
   an attachment device configured to secure the wearable device to the user's wrist such that the wearable device can apply the stimulus to an inner wrist of the user; and
   one or more controllers for adjusting a frequency, tempo, duration, and/or intensity of the stimulus,
   wherein the wearable device is configured to provide the stimulus to the inner wrist of the user at a rate that is faster or slower than a current heart rate of the user to thereby provide the relaxing or stimulating effect.

14. An apparatus as claimed in claim 13, wherein the beat is a single beat.

15. An apparatus according to claim 13, further comprising a capacitive sensor, switches, and/or buttons, configured to enable tactile and/or gestural interaction by the user with the apparatus.

16. An apparatus according to claim 13, wherein the wearable device comprises a piezo-electric actuator, a shape changing material, a linear actuator, or a pneumatic or hydraulic actuator configured for delivering the stimulus.

17. An apparatus according to claim 13, further comprising a visual or audio output in synchrony with the stimulus.

18. An apparatus according to claim 13, further comprising a heart rate monitor.

19. An apparatus according to claim 18, wherein the heart rate monitor is configured to monitor the user's heart rate either in real-time or records the user's heart rate, and wherein the one or more controllers controls the stimulus based on either the monitored real-time heart rate or the recorded heart rate.

20. An apparatus according to claim 18, wherein the heart rate monitor is integrated into the wearable device or separate from the wearable device.

21. An apparatus according to claim 13, further comprising a data input and/or output to enable the apparatus to connect wirelessly, or via a wire, to an external controller or monitor, in order to alter settings for the stimulus.

22. A system comprising the apparatus of claim 13 and an external controller or monitor.

23. An apparatus according to claim 18, wherein a controller of the one or more controllers is capable of altering the stimulus in response to a monitored heart rate of the user.

24. An apparatus for providing a relaxing or stimulating effect on a user, the apparatus comprising:
a wearable device configured to engage the user's skin and to provide a rhythmic tactile stimulus to the user;
an attachment device configured to secure the wearable device to the user's wrist such that the wearable device can apply the stimulus to an inner wrist of the user; and
one or more controllers for adjusting a frequency, tempo, duration, and/or intensity of the stimulus, the one or more controllers being configured to provide the stimulus as a beat that is a double-peaked pulse that substantially matches the form of a human heartbeat,
wherein the wearable device is configured to provide the stimulus to the inner wrist of the user at a rate that is faster or slower than a current heart rate of the user to thereby provide the relaxing or stimulating effect.

* * * * *